(12) United States Patent
Pilato et al.

(10) Patent No.: US 11,594,303 B2
(45) Date of Patent: Feb. 28, 2023

(54) METHOD AND SYSTEM FOR NORMALIZATION OF GENE NAMES IN MEDICAL TEXT

(71) Applicant: KONINKLIJKE PHILIPS N.V., Eindhoven (NL)

(72) Inventors: Samuel Frank Pilato, Cambridge, MA (US); Alexander Ryan Mankovich, Somerville, MA (US); Yong Mao, Eindhoven (NL); Woei-Jye Yee, Boston, MA (US); Qingxin Wu, Lexington, MA (US); Robbert Christiaan van Ommering, Cambridge, MA (US); Weijian Qin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 71 days.

(21) Appl. No.: 17/272,598

(22) PCT Filed: Aug. 13, 2019

(86) PCT No.: PCT/EP2019/071747
§ 371 (c)(1),
(2) Date: Mar. 1, 2021

(87) PCT Pub. No.: WO2020/043487
PCT Pub. Date: Mar. 5, 2020

(65) Prior Publication Data
US 2021/0319854 A1    Oct. 14, 2021

Related U.S. Application Data

(60) Provisional application No. 62/723,717, filed on Aug. 28, 2018.

(51) Int. Cl.
*G16B 50/10* (2019.01)
*G06F 40/284* (2020.01)
*G06F 40/166* (2020.01)

(52) U.S. Cl.
CPC ........... *G16B 50/10* (2019.02); *G06F 40/166* (2020.01); *G06F 40/284* (2020.01)

(58) Field of Classification Search
CPC ...... G06F 40/166; G06F 40/284; G16B 50/10
See application file for complete search history.

(56) References Cited

U.S. PATENT DOCUMENTS 6,263,333 B1    7/2001  Houchin et al.
2008/0208837 A1  8/2008  Wang
(Continued)

FOREIGN PATENT DOCUMENTS

CN    108039943 A   *  5/2018  ........... G06F 16/245
WO    WO-2009135417 A1 * 11/2009  ............. H04L 45/00

OTHER PUBLICATIONS

International Search Report and Written Opinion for International Application No. PCT/EP2019/071747, filed Aug. 13, 2019, 17 pages.
(Continued)

*Primary Examiner* — Chau T Nguyen (57) ABSTRACT

A method (100) for standardizing gene nomenclature, comprising: (i) receiving (110) a source; (ii) tokenizing (120) the source; (iii) comparing (130) a first token to a prefix tree structure with a root node, edges, and leaf nodes; (iv) determining (140) which edge extending from the root node to associated first leaf nodes the first token matches; (v) updating (150) an identification pointer with the location of the first leaf node; (vi) determining (160) which of one or more edges that a second token matches; (vii) updating (170) the identification pointer with the location of the second leaf node; (viii) repeating (172) the determining
(Continued)

(160) and updating (170) steps with subsequent tokens until a subsequent token fails to match an edge extending from a leaf node or there is no edge extending from the leaf node; and (ix) providing (180) an identification of a canonical gene name.

20 Claims, 5 Drawing Sheets

(56) References Cited

U.S. PATENT DOCUMENTS

| | | | |
|---|---|---|---|
| 2011/0055233 A1 | 3/2011 | Weber et al. | |
| 2015/0073719 A1* | 3/2015 | Glynias | G16B 50/10 |
| | | | 702/19 |
| 2016/0012020 A1* | 1/2016 | George | G06F 40/242 |
| | | | 704/9 |
| 2017/0091164 A1* | 3/2017 | Bao | G06F 40/284 |
| 2020/0125563 A1* | 4/2020 | Fan | G06F 16/2246 |

OTHER PUBLICATIONS

Tanenblatt, et al., "The ConceptMapper Approach to Named Entity Recognition", Jan. 1, 2010, Conference Proceedings of the International Concept on Language Resources and Evaluation, pp. 546-551.

Murphy, et al., Human Gene Name Normalization using Text Matching with Automatically Extracted Synonym Proceedings of the BioNLP Workshop on Linking Natural Language Processing and Biology at HLT-NAACL 06, pp. 41-48.

Hu, et al., "Integrating Various Resources for Gene Name Normalization", PLOS ONE, Sep. 2012, vol. 7, Issue 1-9.

* cited by examiner

METHOD AND SYSTEM FOR NORMALIZATION OF GENE NAMES IN MEDICAL TEXT

RELATED APPLICATIONS

This application is the U.S. National Phase application under 35 U.S.C. § 371 of International Application No. PCT/EP2019/071747, filed on Aug. 13, 2019, which claims the benefit and priority to Provisional Application No. 62/723,717, filed Aug. 28, 2018, which is incorporated by reference in its entirety.

FIELD OF THE DISCLOSURE

The present disclosure is directed generally to methods and systems for recognizing and normalizing gene names.

BACKGROUND

Given an accelerating focus on precision medicine, including increasing numbers of clinical trials targeting the therapeutic treatment of patients with particular genetic variants, the extraction of pertinent information from patient medical records and clinical trial descriptions must include identification and extraction of mentions of particular genetic tests and variants.

A gene name is typically a mention in medical text intended to identify a specific gene. Such a mention functions like a noun phrase within text, and its internal composition respects the sensibilities of English or other natural language. But its nomenclature often consists of highly-technical molecular and clinical vocabulary, sub-specialty notations, other jargon, and acronym-like symbols. Thus, the gene name is typically a hybrid between natural language and a special notation. Recognizing a gene name involves locating the mention, classifying it as a gene name, and identifying the specific referenced gene.

In addition to recognizing a gene name, there are benefits to normalizing gene names. Normalizing a gene name typically requires an understanding of the range of possible mentions which identify the same gene, appreciating or determining that one of those mentions is the preferred representative for that range (the "canonical name"), and associating the observed mention with its preferred representative.

There are existing systems that attempt to deal with recognition and normalization of gene names. For example, there are multiple specifications and standards for gene nomenclature, multiple databases of gene names and relationships among them, and multiple machine-learning systems that marry naming rules, database entries, and actual naming patterns in text corpora. However, the recall and precision percentages for these methods typically reach the high 70's at best in practice, as gene naming patterns and contexts are highly productive and continue to evolve. Thus, gene name recognizers/normalizers entail dependencies on external sources and tools, and require complex mechanisms and data, yet provide modest performance.

SUMMARY OF THE DISCLOSURE

There is a continued need for methods and systems that, with greater accuracy and efficiency, recognize the wide variety of nomenclature associated with gene names and convert these gene name variations into a canonical form. Various embodiments and implementations herein are directed to a method and system configured to identify canonical gene names for gene identifiers found in a variety of possible sources. The system tokenizes text from a source into a token stream, and compares a first token from the token stream to a data structure generated from a database of gene identifiers and corresponding canonical gene name for each of a plurality of genes. The data structure is a prefix tree structure with a root node, a plurality of edges, and a plurality of leaf nodes. To identify gene identifiers in the token stream, and the canonical name associated with an identified gene identifier, the system determines which of a plurality of edges extending from the root node to associated first leaf nodes the first token matches. If the token matches any of the plurality of edges, an identification pointer tasked with facilitating identification of a canonical gene name is updated with the location of the first leaf node associated with the matching edge. The token then traverses the tree structure, updating the identification pointer. For example, the system determines which, if any, of a plurality of edges extending from the first leaf node to second leaf nodes that a second, subsequent token from the token steam matches. If the second token matches an edge extending from the first leaf node, the identification pointer is updated with the location of the second leaf node associated with the matching edge. This is repeated with subsequent tokens from the token stream using extending edges and nodes until a subsequent token fails to match an edge extending from a leaf node. When a subsequent token fails to match an edge extending from a leaf node, an identification of the canonical gene name is provide based on the most recent location of the identification pointer.

Generally, in one aspect, a method for standardizing gene nomenclature is provided. The method includes: (i) receiving a source comprising one or more gene identifiers; (ii) tokenizing text from the source into a token stream; (iii) comparing a first token from the token stream to a data structure generated from a database of gene identifiers and corresponding canonical gene name for each of a plurality of genes, the data structure comprising a prefix tree structure with a root node, a plurality of edges, and a plurality of leaf nodes; (iv) determining which of one or more edges extending from the root node to associated first leaf nodes the first token matches; (v) updating an identification pointer with the location of the first leaf node associated with the matching edge; (vi) determining which, if any, of one or more edges extending from the first leaf node to second leaf nodes that a second, subsequent token from the token steam matches; (vii) updating, if the second token matches an edge extending from the first leaf node, the identification pointer with the location of the second leaf node associated with the matching edge; (viii) repeating the determining and updating steps with subsequent tokens from the token stream using any additional extending edges and leaf nodes until a subsequent token fails to match an edge extending from a leaf node or there is no edge extending from the leaf node; and (ix) providing, when a subsequent token fails to match an edge extending from a leaf node, or if there is no edge extending from the leaf node, an identification of a canonical gene name based on a most recent location from the identification pointer.

According to an embodiment, the method further includes generating a curated table of gene identifiers and associated canonical gene names; tokenizing the curated table into a token stream; and generating, using the token stream, the prefix tree structure.

According to an embodiment, tokenization of the curated table into a token stream and the tokenization of text from the source into a token stream utilizes the same tokenization logic.

According to an embodiment, the method further includes: generating a list of most common words in a language; comparing the list of most common words to the gene identifiers in the curated table; and identifying any gene identifiers found in the list of most common words.

According to an embodiment, providing an identification of a canonical gene name based on a most recent location from the identification pointer comprises updating the identification pointer with a location of a leaf node upstream of the most recent matching leaf node.

According to an embodiment, the method further includes the step of determining whether the identified canonical gene name is also common natural language word.

According to an embodiment, tokenization comprises generating an acronym for every capitalized phrase in a document, and preventing or removing each occurrence of a generated acronym from the token stream.

According to an embodiment, tokenization comprises generating a single token of each string of Roman letters, generating a single token of each run of numbers, and generating a single token with each Greek letter.

According to an embodiment, providing an identification of a canonical gene name comprises information about a location of a gene identifier in the source.

Generally, in a second aspect, is a system for standardizing gene nomenclature. The system includes: a source comprising one or more gene identifiers; a data structure generated from a database of gene identifiers and corresponding canonical gene name for each of a plurality of genes, the data structure comprising a prefix tree structure with a root node, a plurality of edges, and a plurality of leaf nodes; and a processor configured to: (i) tokenize text from the source into a token stream; (ii) compare a first token from the token stream to the data structure; (iii) determine which of one or more edges extending from the root node to associated first leaf nodes the first token matches; (iv) update an identification pointer with the location of the first leaf node associated with the matching edge; (v) determine which, if any, of one or more edges extending from the first leaf node to second leaf nodes that a second, subsequent token from the token steam matches; (vi) update, if the second token matches an edge extending from the first leaf node, the identification pointer with the location of the second leaf node associated with the matching edge; (vii) repeat the determining and updating with subsequent tokens from the token stream using any additional extending edges and leaf nodes until a subsequent token fails to match an edge extending from a leaf node or there is no edge extending from the leaf node; and (viii) provide, when a subsequent token fails to match an edge extending from a leaf node, or if there is no edge extending from the leaf node, an identification of a canonical gene name based on a most recent location from the identification pointer.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the various embodiments will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure describes various embodiments of a system and method configured to locate a canonical gene name for a wide variety of gene identifiers found in a variety of possible sources. More generally, Applicant has recognized and appreciated that it would be beneficial to provide a system that more accurately and more efficiently identifies canonical gene names. The system tokens information from a document or other source, and compares a first token from the token stream to a data structure generated from a database of gene identifiers and corresponding canonical gene name for each of a plurality of genes. The data structure is a prefix tree structure with a root node, a plurality of edges, and a plurality of leaf nodes. To identify gene identifiers in the token stream, and the canonical name associated with an identified gene identifier, the system determines which of a plurality of edges extending from the root node to associated first leaf nodes the first token matches. If the token matches any of the plurality of edges, an identification pointer tasked with facilitating identification of a canonical gene name is updated with the location of the first leaf node associated with the matching edge. The token then traverses the tree structure, updating the identification pointer. For example, the system determines which, if any, of a plurality of edges extending from the first leaf node to second leaf nodes that a second, subsequent token from the token steam matches. If the second token matches an edge extending from the first leaf node, the identification pointer is updated with the location of the second leaf node associated with the matching edge. This is repeated with subsequent tokens from the token stream using extending edges and nodes until a subsequent token fails to match an edge extending from a leaf node. When a subsequent token fails to match an edge extending from a leaf node, an identification of the canonical gene name is provide based on the most recent location of the identification pointer.

Recognizing gene identifiers, and standardizing these gene identifiers to a canonical name, presents a wide array of challenges. For example, matching methods typically used for natural languages don't work well for nomenclature incorporating special notations. There are fewer kinds of variation available that preserve equivalence, and in non-word codes, the change of even a single letter or digit could change the meaning. Additionally, a phrasal gene name may contain an internal word for which equivalent synonyms may be substituted without changing the gene identifier (such as " . . . iron-sulfur . . . " to " . . . Fe—S . . . "). In some cases, a generic internal word in a gene identifier may be optional and subject to dropping entirely.

A gene identifier may contain an internal non-word notation for which equivalent synonyms may be substituted without changing the identity of the identifier. For example, within specific contexts, the Greek small letter β may be replaced with the Roman letter B or with the Roman letter name beta. For example, the same gene may be called "TGF β-1," "TGFB1," "TGFbeta," and "transforming growth factor, beta 1."

A gene identifier may contain a punctuation mark which may be replaced with a different punctuation mark or with a space, or even dropped entirely, without changing the gene identifier. A final "+" or "−" (such as "HER2+") indicates behavior or presence, thus is not part of the gene name. In contrast, a parenthesized subexpression may be wholly internal or name-initial or name-final, and is part of the gene identifier. For example, gene identifiers such as "P138 (TOX)" and "C-P4Halpha(II)" are not readily tokenized or recognized by automated systems. A small gene identifier may be hyphenated with a non-name word, such as "BRAF-related," "p53-defective," "non-CCND 1 cohort," "HER2-overexpressing," "HER2-positive," and "progesterone receptor-modulation," or with a separate gene name, such as describing a fusion among other examples. As another example, variations in Roman letter casing may stray from proper and facile standards without changing the identity of the referent.

In addition, multiple genes may be jointly mentioned via a distributive expression over pieces of gene identifiers. The expression indicates a pair or list or disjunction or conjunction of genes whose separate names must be reconstructed. Examples include "CCR2/5," "HLA-A, B, or C," and "HLA-A, B, C, DRB1, and DQB1."

Another issue faced when recognizing gene identifiers is that an acronym-like gene symbol may also be a word in English or other natural language, or may also be an acronym referring to some non-gene/non-protein referent. Often, context outside the gene identifier itself may be required for disambiguation and proper identification. For example, the sentence "Diffusion capacity of the lung for carbon monoxide (DLCO)<40% (corrected), total lung capacity (TLC)<40%, forced expiratory volume in one second (FEV1)<40% and/or receiving supplementary continuous oxygen" does not comprise any gene identifiers as shown by the context of the abbreviations, although many automated systems would identify DLCO, TLC, and/or FEV1 as gene identifiers.

In addition to gene identifier recognition, gene name standardization or canonicalization presents several issues. For example, gene name standardization requires a master knowledge source rather than the many different sources of gene name. Having multiple sources leads to distinct gene identifiers which are not relatable by any rule-bound transformations and not sufficiently learnable from contextual statistics.

In addition, a non-canonical gene name may be ambiguous with respect to which gene it refers to. That is, the mentioned name itself may have more than one candidate canonical name, depending on which gene it refers to. Context outside the mention itself is required for disambiguation. Thus, though a gene has a unique canonical name, a gene name may map to multiple canonical names. This ambiguity remains even when the universe of gene names is restricted to exclude references to explicitly non-human genes.

Accordingly, the gene name identification systems and methods described or otherwise envisioned herein specifically address these and other known issues relating to the recognition and standardization of gene identifiers.

Figure 1:
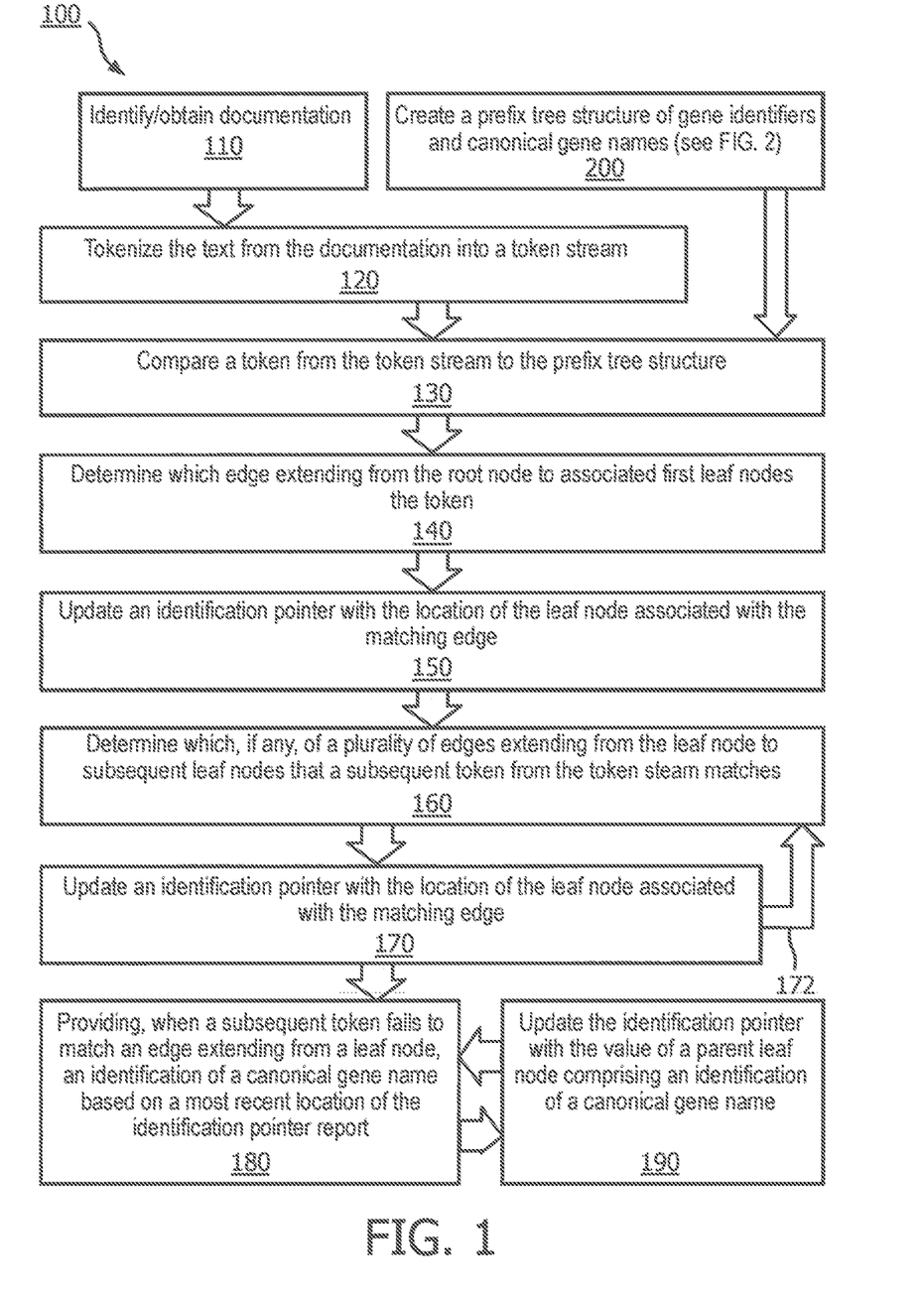
FIG. 1 is a flowchart of a method for identifying canonical gene names, in accordance with an embodiment.

Referring to FIG. 1, in one embodiment, is a flowchart of a method 100 for identifying canonical gene names in tokenized sources using a gene name identification system. The methods described in connection with the figures are provided as examples only, and shall be understood not to limit the scope of the disclosure. The gene name identification system can be any of the systems described or otherwise envisioned herein.

At step 110 of the method, one or more documents or other sources are obtained or received by the gene name identification system. These documents or other sources can be any text, document, or other record or source comprising text or images. According to a preferred embodiment, the sources are digital or digitized sources. For example, the sources may be journals, databases, clinical information, lab reports, and/or any other information that may contain or is likely to contain a gene identifier. These are just examples and not meant to be exhaustive. The sources can be provided to the gene name identification system by an individual or another system. Additionally and/or alternatively, the sources can be retrieved by the gene name identification system. For example, the gene name identification system may continuously or periodically access a database, website, or any other resource comprising or providing sources. As just one example, the gene name identification system may access a private or public repository of research articles, such as PubMed or any other database.

The received or obtained sources may be stored in a local or remote database for use by the gene name identification system. For example, the gene name identification system may comprise a database to store the sources, and/or may be in communication with a database storing the sources. These databases may be located with the gene name identification system or may be located remote from the gene name identification system, such as in cloud storage and/or other remote storage.

At step 120 of the method, gene name identification system tokenizes information from the obtained or received documents or other sources. The gene name identification system may prepare a source for tokenization using any method or system for processing that facilitates downstream text-based analysis. This processing may include, for example, identification and/or extraction of text from the source, especially if the source comprises content other than text such as images, tables, or other non-text content. The processing may also include normalization of the extracted text, translation of extracted text, and many other forms or kinds of processing. The processed text-based sources, or the processed content therein, may be stored in local or remote storage for subsequent steps of the process. The gene name identification system may process each text-based source as it is received, or may process text-based sources in batches, or may process a text-based source just before it is analyzed in a subsequent step of the method.

As described herein or otherwise recognized, gene identifiers can come in an unlimited number of formats and variations, and thus suitable tokenization is a vital step in recognition and standardization of gene identifiers. Accordingly, the gene name identification tokenizer is configured to tokenize data from the obtained or received documents or other sources in a manner that optimizes gene identifier recognition. A variety of tokenizers and/or tokenization methods may be utilized.

According to an embodiment, the tokenizer comprises one or more of the following settings, configurations, or thresholds. The tokenizer may be configured to construct a single token of each occurrence of non-genomic special notations such as times, dates, and numbers. The tokenizer may be configured to generate a single token of each run of Roman letters, and separately of each run of digits. For example, the phrase MEKK4 may be tokenized to generate tokens "MEKK" and "4".

According to an embodiment, the tokenizer may be configured to generate a token of each Greek letter or other special notation. Accordingly, the gene identifier p38α may be tokenized as "p", "38", and "α". The tokenizer may be configured to generate a token of all other remaining characters, while generating a token of every flow-breaking run of whitespace, thereby generating a paragraph mark. According to an embodiment, all other whitespace is removed from the token stream. In some embodiments or variations, spaces may be optional.

According to an embodiment, the other remaining characters may be further processed. For example, the tokenizer may be configured to filter out some punctuation tokens such as hyphens. The tokenizer may be configured to fold the case of all Roman letters into all lower-case. For example, "MEKK" may be tokenized as "mekk". The tokenizer may also be configured to fold each Roman name of a Greek letter into the Greek letter itself. For example, p38alpha may be tokenized as "p", "38", and "α".

According to an embodiment, the tokenizer may comprise a lightweight parser for composing lists of conjuncts or disjuncts, via iterative operations such as "Xs←X" and "Xs←Xs (,)? (and)? X", among many others.

The tokenizer or tokenization instructions may utilize a wide variety of mechanisms to facilitate improved tokenization of gene identifiers, which subsequently improves canonical gene name identification. Tokenization may encounter difficulties, for example, when encountering optional internal words, synonym substitutions, the substitution of a Roman letter for a Greek letter, and ambiguity with non-gene acronyms.

According to an embodiment, the tokenizer may filter out non-gene acronyms by generating acronyms for each capitalized phrase in the same text as though it is a proper name, and commandeering any occurrences of those mistaken for gene names. According to an embodiment, the tokenizer may manage optional and synonymous words by simple token-level filtering and folding, here at the word level with a small vocabulary. According to another embodiment, the tokenizer may utilize heuristics to substitute Roman for Greek letters, such as trying only a Roman letter not followed by another letter. For other cases, the system may add appropriate entries to the curated table.

At step 130 of the method, the gene name identifier system compares a token from the token stream to a data structure configured to facilitate gene name recognition. According to an embodiment, the data structure is a prefix tree structure comprising gene identifiers and associated canonical gene names. The data structure, such as the prefix tree structure, may be constructed or otherwise generated using any method or system.

Figure 2:
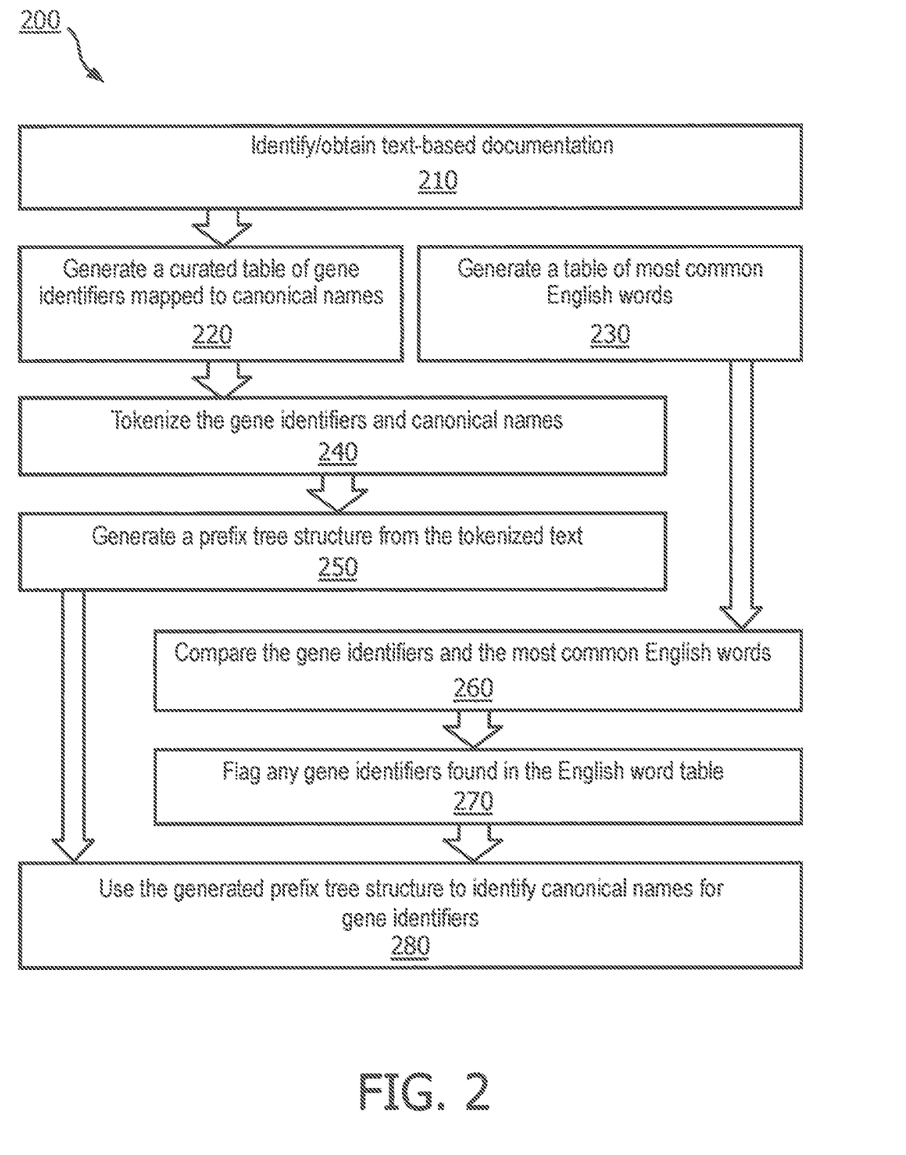
FIG. 2 is a flowchart of a method for creating a gene identifier tree structure, in accordance with an embodiment.

Referring to FIG. 2, in one embodiment, is a method 200 for generating a data structure configured to facilitate gene name recognition, and specifically for creating a prefix tree structure of gene identifiers and canonical gene names.

At step 210 of the method, one or more documents or other sources are obtained or received by the gene name identification system and utilized to identify gene identifiers and canonical names. These documents or other sources can be any text, document, or other record or source comprising text or images that facilitate the identification of gene identifiers and canonical names for the data structure. For example, this may be a corpus of documents from journals, databases, clinical information, lab reports, and/or any other information that may contain or is likely to contain a gene identifier. The sources can be provided to the gene name identification system by an individual or another system. Additionally and/or alternatively, the sources can be retrieved by the gene name identification system. The received or obtained sources may be stored in a local or remote database for use in the method.

At step 220 of the method a curated table of gene identifiers, each mapped to its canonical gene name, is constructed. The table can be partially or completely generated manually by reviewers or other individuals tasked with associating gene identifiers and canonical gene names. Some gene identifiers may map to multiple canonical gene names, and some canonical gene name may map to multiple gene identifiers. Many other variations are possible.

According to an embodiment, gene identifiers on either side of the mapping (i.e., either gene identifiers or canonical names) may be phrasal, meaning they consist of multiple terms or words or symbols in sequence. The table may be any size suitable for the method, and may depend on the organism from which the gene names are being canonicalized, as well as on the variety of gene names generated for that organism, among many other features. For example, the total number of gene identifiers and canonical gene names in a table may number in the hundreds, thousands, or hundreds of thousands. Although this information is identified and described as a "table," it should be recognized that the information can be organized and/or stored in a variety of different formats and data structures.

Referring to TABLE 1 is an example of a portion of a data structure comprising a list of gene identifiers and canonical gene names. In this example, four different gene identifiers "ajuba LIM protein", "JUB", "jub, ajuba homolog (*Xenopus laevis*)", and "MGC15563" all refer to the canonical gene name "AJUBA". Accordingly, each of the four different gene identifiers is associated in the table with the canonical gene name "AJUBA". Due to this association of the data in this table or other data structure, identification of any of the four different gene identifiers will subsequently identify the associate canonical gene name "AJUBA".

TABLE 1

Table of Gene Identifiers and Associated Canonical Gene Names

| Gene Identifier | Canonical Gene Name |
|---|---|
| ajuba LIM protein | AJUBA |
| JUB | AJUBA |
| jub, ajuba homolog (Xenopus laevis) | AJUBA |
| MGC15563 | AJUBA |

The table or data structure may be stored in a local or remote database for use by the gene name identification system. For example, the gene name identification system may comprise the data structure, and/or may be in communication with a memory comprising the data structure.

Accordingly, data structure may be located with the gene name identification system or may be located remote from the gene name identification system, such as in cloud storage and/or other remote storage.

At step 240 of the method, the gene identifiers and canonical names in the table are tokenized. According to an embodiment, the tokenizer utilized to generate the data structure is the same tokenizer, or utilizes the same logic, as the tokenizer utilized to generate the token stream for gene name standardization in step 120 of the method. According to another embodiment, the tokenizer utilized to generate the data structure comprises one or more differences from the tokenizer utilized to generate the token stream.

At step 250 of the method, a data structure is generated from the tokenized information from the table of gene identifiers and canonical gene names. According to an embodiment, the data structure is a prefix tree structure, and the keys of the prefix tree structure are the token sequences. As the data structure is being generated, according to an embodiment, when a tokenized gene identifier is added to the data structure but the canonical gene name already exists in the table, the value of the tokenized gene identifier will be added to the existing value for that key. Thus, each gene identifier will map to a set of canonical names rather than each gene identifier mapping to a single canonical name, as demonstrated in TABLE 1. According to an embodiment, after all key/value pairs are loaded into the data structure, a closure is performed by mapping each canonical name to itself. These and other variations of the construction of the data structure are possible.

Figure 3:
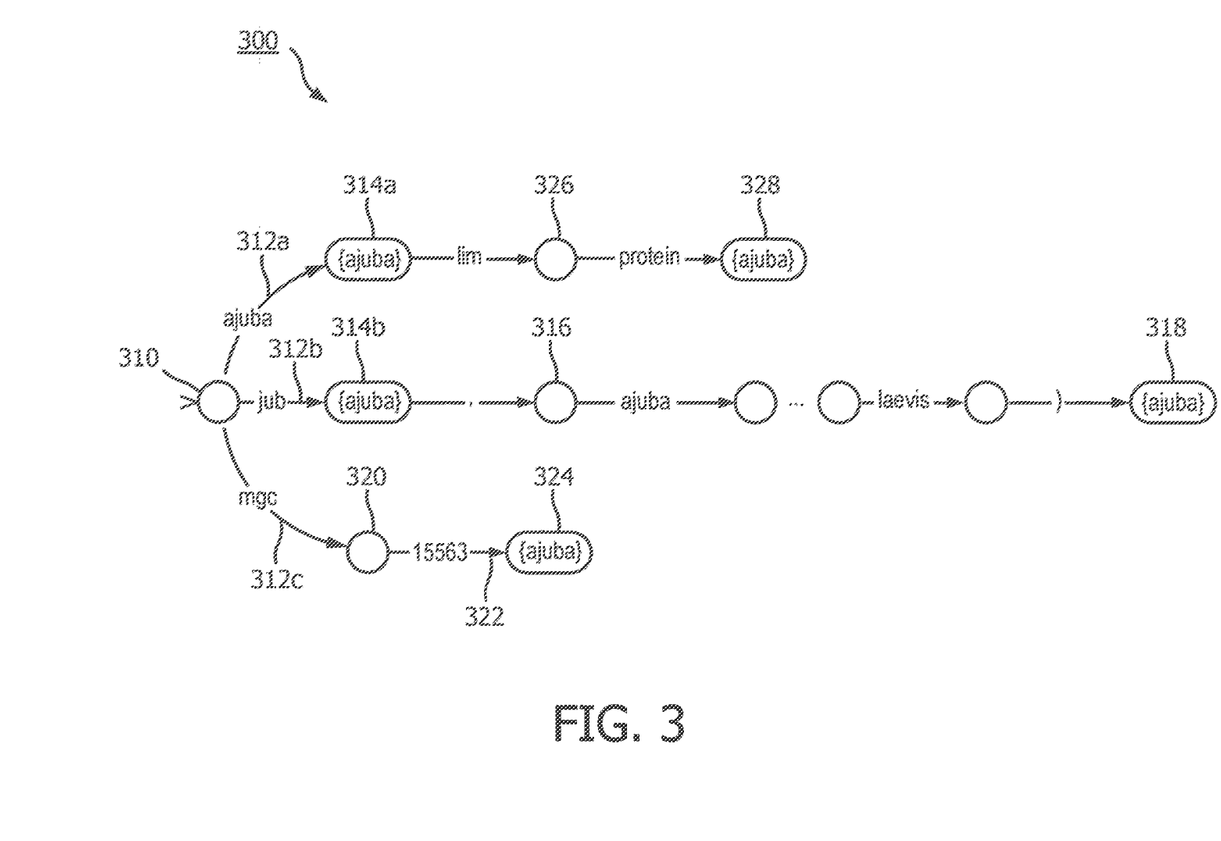
FIG. 3 is a gene identifier tree structure, in accordance with an embodiment.

Referring to FIG. 3, in one embodiment, is a portion 300 of a generated or loaded tree structure using tokenized information from TABLE 1. This generated or loaded tree structure is meant only as an example and thus does not limit the scope of the disclosure. In this isolated portion of an overall tree structure, node 310 can be representative of a root node. Each of the edges 312a, 312b, and 312c are loaded with or comprise one of the three possible tokens recognized by (and, as discussed herein, generated by) the system based on TABLE 1, namely "ajuba", "jub" (since "JUB" and "jub" are equivalent in an embodiment in which all Roman letters are converted to lowercase during tokenization), and "MGC".

Edges 312a and 312b each lead to a leaf node 314a and 314b, respectively, each comprising a word or symbol in the respective gene identifier. For example, since both "ajuba" and "jub" may effectively positively identify the canonical gene name AJUBA, the value of leaf nodes 314a and 314b is the canonical gene name AJUBA. However, the tree structure is configured to handle subsequent tokens if they comprise additional components of possible gene identifiers for AJUBA. For example, the token "jub" may be a lone gene identifier that identifies the canonical gene name AJUBA, while the token "jub" may also be the first token in a string of tokens extracted from "jub, ajuba homolog (*Xenopus laevis*)". Thus, if the next token in the string is "," (a comma) then the token matches the edge extending from leaf node 314b to leaf node 316, which is a placeholder indicating the space between the "," and "ajuba" in the phrase "jub, ajuba homolog (*Xenopus laevis*)". The placeholder also indicates that the tree structure was constructed with additional possible information from a gene identifier, although a positive identification as the canonical gene name AJUBA can already be made due to leaf node 314b. Each string terminates in a leaf node comprising the canonical gene name, such as leaf node 318 comprising the canonical gene name AJUBA.

At step 230 of the method, the system generates a table or other data structure comprising a list of some of the most commonly used English (or other language) words. This can be accomplished, for example, by identifying or retrieving a public or private ranking or other list of the most common English (or other language) words based on usage. According to an embodiment, the listing may be based on specific uses such as within scientific literature, among many other possibilities. The number of words included in the table or other data structure may be determined by a variety of factors including one or more user settings, the source of the information, and/or other factors. For example, the number of words included in the table or other data structure may be in the hundreds, thousands, or hundreds of thousands.

At step 260 of the method, the gene identifiers from the table are compared to the table or other data structure comprising the list of most commonly used English (or other language) words. This can be accomplished, for example, using any method of comparing two data sources. At step 270 of the method, the system identifies and/or flags any words that are found to be both a gene identifier and as a most commonly used English (or other language) word. This list can be utilized when performing gene identification and canonicalization, as described or otherwise envisioned herein.

At step 280 of the method, the generated prefix tree structure can be used to identify canonical names for gene identifiers, as described or otherwise envisioned herein. The data structure may be stored in a local or remote database for use by the gene name identification system. For example, the gene name identification system may comprise the data structure, and/or may be in communication with a memory comprising the data structure. Accordingly, data structure may be located with the gene name identification system or may be located remote from the gene name identification system, such as in cloud storage and/or other remote storage.

Returning to FIG. 1, at step 140 of the method the gene name identification system determines, based on the comparison at step 130, which of the plurality of edges extending from the root node to associated first leaf nodes the first compared token matches. This determination may be performed using any method or algorithm for comparing two data points and identifying a match. According to an embodiment, an exact match may be required, and/or there may be fuzziness allowed in the match, which can be based on a user setting, a configuration of the system, and/or any other source. Referring to portion 300 of a tree structure in FIG. 3, as just one example of an embodiment, the system determines which of the plurality of edges 312a, 312b, and 312c extending from this representative root node 310 the first token matches. If the token matches one of edges 312a, 312b, and 312c, the gene name identification system determines that there is a match and the method can progress to the next step.

Referring to portion 300 of a tree structure in FIG. 3, in one embodiment, the token "mgc" (from the gene identifier MGC15563) is a portion of the token stream being compared to the prefix data structure. The "mgc" token matches edge 312c, and thus the system determines that there is a match between this token and this edge.

At step 150 of the method, an identification pointer is updated with the location, value, or other indicator of the most recent leaf node identified by the system using the token stream. The identification pointer can be any pointer, data point, or other mechanism for recording or otherwise notifying or locating a location along the data structure 300. For example, the identification pointer can be a cached data point which is updated with each newly-identified or traversed leaf node. The default value of the identification pointer may be the root node of the data structure, and may be updated only if there is a match between a token and an edge extending from the root node to a leaf node. According to an embodiment, the identification pointer is used to identify a canonical gene name associated with a gene identifier.

For example, referring to FIG. 3 in which the token "mgc" matches edge 312c, the identification pointer is updated with the value, location, or other indicator of leaf node 320. Since leaf node 320 does not comprise a canonical gene name, this value of the identification pointer does not yet identify a canonical gene name.

At step 160 of the method, the system compares the next token from the token stream to the one or more edges extending from the current leaf node to determine which, if any, of these one or more edges the next token matches. This determination may be performed using any method or algorithm for comparing two data points and identifying a match. According to an embodiment, an exact match may be required, and/or there may be fuzziness allowed in the match, which can be based on a user setting, a configuration of the system, and/or any other source. Referring again to portion 300 of a tree structure in FIG. 3, in one embodiment, the first token ("mgc") identified leaf node 320. The next token ("15563") is compared to the one edge 322 extending from leaf node 320 to determine whether there is a match between the edge 322 and token "15563". The system determines that there is a match in this example.

At step 170 of the method, the identification pointer is updated with the location, value, or other indicator of the new leaf node identified by the system using the token stream. For example, if the identification pointer is a cached data point which is updated with each newly-identified or traversed leaf node, the data point is updated with the new leaf node information. Referring again to portion 300 of a tree structure in FIG. 3, in one embodiment, in which the token "15563" matches edge 322, the identification pointer is updated with the value, location, or other indicator of leaf node 324. In this example, the value or location of leaf node 324 is ajuba, the canonical gene name for the gene identifier MGC15563 which was tokenized as "mgc" and "15563".

At 172 of FIG. 1, steps 160 and 170 are optionally repeated until subsequent tokens from the token stream using any additional extending edges and leaf nodes until a subsequent token fails to match an edge extending from a leaf node or there is no edge extending from the leaf node. For example, the most recent leaf node traversed by the most recent token—and thus the most recent location or value of the identification pointer—may be the terminus of a branch of the tree, in which case there are no extending edges. Alternatively, the next token in a token stream may not match any of the one or more edges extending from the leaf node, because some members of the family of gene identifiers for a canonical gene name includes optional additional wording, symbols, numbers, or other terminology not found in all of the gene identifiers, or because the token might be a previously-unknown or uncategorized gene identifier within this family of gene identifiers, or because it might be a separate word or subsequent gene identifier not associated with the previous gene identifier, among many other reasons.

Referring again to portion 300 of a tree structure in FIG. 3, in one embodiment, the identification pointer had been most recently updated with the value, location, or other indicator of leaf node 324, the value of which is ajuba, the canonical gene name for the gene identifier MGC15563. In this example, leaf node 324 is the terminus of this branch of tree 300, and thus there are no edges extending from leaf node 324. Accordingly, there are no more edges or leaf nodes to traverse and the identification pointer comprises the terminus value of this branch, or the canonical gene name.

At step 180 of the method, when a subsequent token fails to match an edge extending from a matching leaf node, or if there is no edge extending from the matching leaf node, the system provides or otherwise identifies or generates the determined canonical gene name based on a most recent location of the identification pointer, if an identification is possible. For example, if portion 300 of a tree structure in FIG. 3, in one embodiment, was a complete tree and the first token was "mekk" which does not match any of the edges extending from the root node, then the identification pointer would not have been updated and no determined canonical gene name could be identified. The value of the identification pointer might remain the default or might be empty, indicating that no canonical gene name was identified.

According to an embodiment, the determination or value of a canonical gene name can be provided, recorded, reported, or otherwise made available or utilized. For example, the system can provide the value or location of the identification pointer, which may be the determined canonical gene name, to another data point, a table, a report, or other location. For example, the system may create a table or list of all canonical gene names identified in a source. This could be created in memory or a database, displayed on a screen or other user interface, or otherwise provided. The report or list may also comprise the gene identifier or identifiers utilized to identify the canonical gene name, as well as information about the token or location of the token within the analyzed source. A report may be a visual display, a printed text, an email, an audible report, a transmission, and/or any other method of conveying information. The report may be provided locally or remotely, and thus the system or user interface may comprise or otherwise be connected to a communications system. For example, the system may communicate a report over a communications system such as the internet or other network. May other methods of providing, recording, reporting, or otherwise making canonical gene names available, or using the canonical gene names, are possible. According to an embodiment, after the determination or value of a canonical gene name is provided, the identification pointer can be returned to the default or empty value.

The identification pointer may only be updated with a leaf node value if that leaf node comprises a canonical gene name. Alternatively, the identification pointer may be updated with the value of every traversed leaf node, in which case the identification pointer may comprise a value or location that isn't a canonical gene name. Referring to FIG. 3, for example, if the tokens "ajuba" and "lim" had been utilized to update the identification pointer with the value or location of leaf node 326, this value or location is not a canonical gene name. If the next token in the token stream is "alpha" rather than the expected "protein", then there is not a match with edge 328 and the identification pointer is not updated with any other leaf node value. However, the identification pointer comprises a value or location that is not a canonical gene name. Accordingly, at step 190 of the method, the system updates the identification pointer with the value of a parent or upstream leaf node comprising an identification of a canonical gene name, or otherwise reports the value or location of this parent or upstream leaf node. Referring again to the example in FIG. 3 where the final value or location of the identification pointer is leaf node 326

(which is not associated with a canonical gene name), the system may direct the identification pointer to be updated with the closest parent or upstream leaf node comprising an identification of a canonical gene name, which would be leaf node 314a with the canonical gene name "ajuba".

According to an embodiment, if a token does not match any edge extending from the root, the system may determine whether to attempt any other annotators or analysis. If not, then the system may discard the token and move to the next token, repeating the method described or otherwise envisioned herein with that next token.

According to an embodiment, if the identified canonical gene name is also a word found in the list of common words, as from the flagged list from step 270 of method 200 in FIG. 2, the identified canonical gene name can be flagged, noted, or otherwise indicated. This may indicate, for example, that the identified canonical gene name is gene-English (or other language) ambiguous, which can complicate the identification and/or standardization.

According to an embodiment, the system may utilize, anywhere that the system has paused or is seemingly at the end of a gene identifier, the lightweight parser for composing or identifying conjuncts or disjuncts. The lightweight parser may utilize, for example, iterative operations such as "Xs←X" and "Xs←Xs (,)? (and)? X", among many others.

Figure 4:
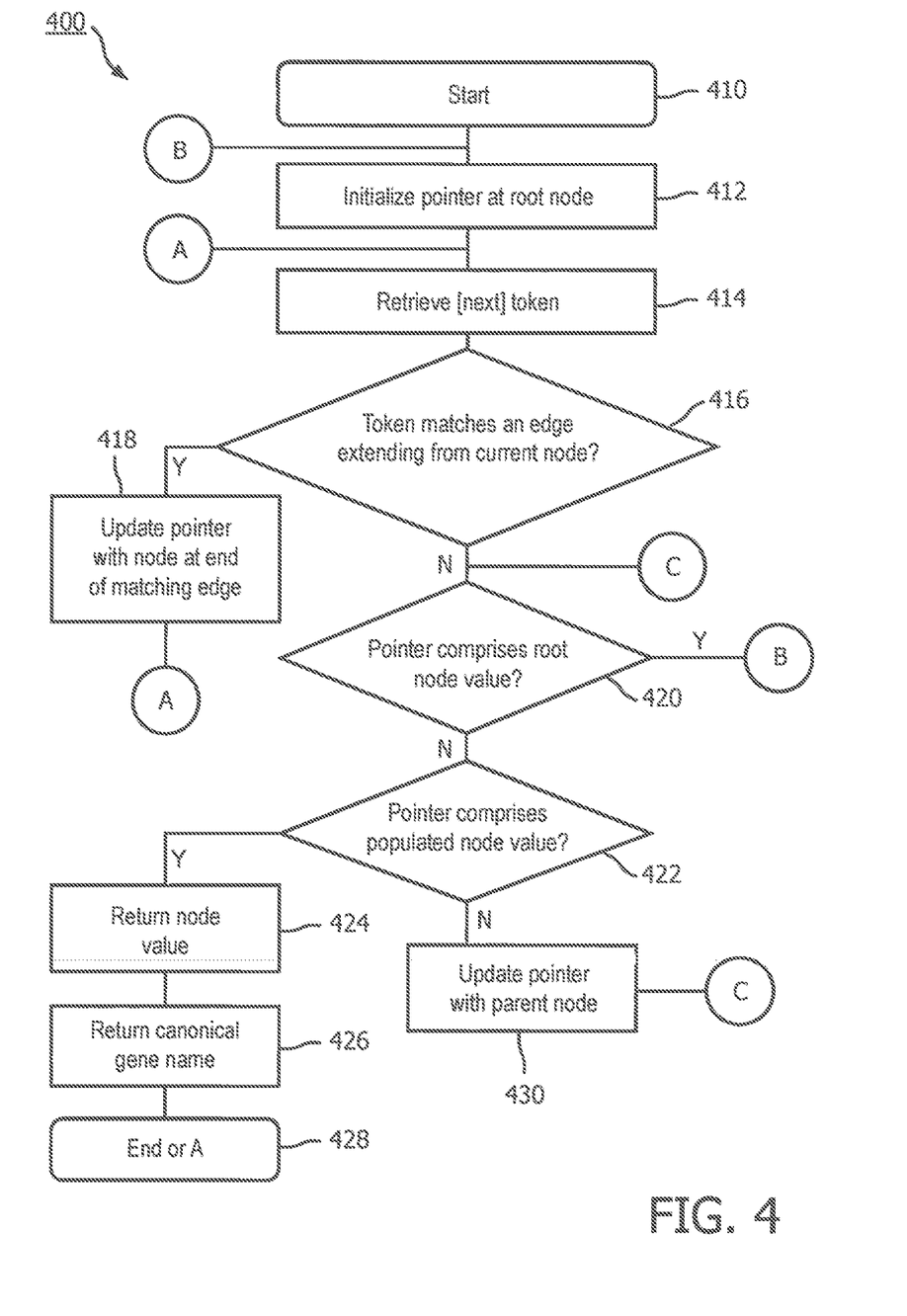
FIG. 4 is a flowchart of a method for identifying canonical gene names, in accordance with an embodiment.

Referring to FIG. 4, in one embodiment, is a decision-making flowchart 400 for identifying a canonical gene name in a tokenized source using a gene name identification system as described or otherwise envisioned herein. The process begins at step 410 with a token stream generated from a source. The source can be any source containing or potentially containing one or more gene identifiers, and the source can be tokenized using any of the methods or protocols described or otherwise envisioned herein.

At 412, the identification pointer is initialized at the root node of the tree-based data structure. This may comprise setting the identification pointer to zero, a default value, or a value of the root node.

At step 414, tokens from the token stream are fed into the system one at a time. If this is the first token from the source, it will be the first time progressing through this flowchart. If this is a second or subsequent token from the token stream, the system will have already progressed through the chart and returned to step 412 or 414 for analysis of the next token.

At step 416, the system determines whether the current token matches any of the one or more edges extending from the current node (which will be the root node for at least the first token), if there are any edges extending from the current node. This determination may be performed using any method or algorithm for comparing the token and the edges to identify a match. According to an embodiment, an exact match may be required, and/or there may be fuzziness allowed in the match, which can be based on a user setting, a configuration of the system, and/or any other source.

At 418, if the current token matches one of the one or more edges extending from the current node, then the identification pointer will be updated with the value or location of the leaf node at the end of the matching edge. The system will then return to step 414, as shown by "A" to process the next token in the token stream.

At 420, if the current token does not match any of the one or more edges extending from the current node, or if there aren't any edges extending from the current node, the system optionally determines whether the identification pointer comprises the root node value. If it is, then the token did not comprise, or is considered to have not comprised, a gene identifier, and the system returns to step 412 as shown by "B" to process the next token in the token stream and ensure that the identification pointer is at the default or initial value.

If the identification pointer does not comprise the root node value, meaning it has been updated one or more times with a value or location of a leaf node using one or more tokens, then at 422 the system determines whether the identification pointer comprises a value or location of a populated leaf node value. As shown in FIG. 3, for example, some leaf nodes such as 316, 320, and 326 do not comprise a canonical gene name value or location, which may represent a placeholder or other information. If the identification pointer comprises a value or location of a populated leaf node value, such as leaf nodes 314a, 314b, or 318 in FIG. 3, then at 424 the system provides the leaf node value from the identification pointer, which is either a canonical gene name or a value or location associated with and thereby identification a canonical gene as shown at 426. The system can either end if the token stream is complete, or the system can return to step 414 as shown by "A" in FIG. 4.

If the identification pointer does not comprise a value or location of a populated leaf node value, then the system progresses to 430 in which case the identification pointer is updated with the value of a parent or upstream node and the system returns to step 420 as shown by "C" in FIG. 4. For example, referring to FIG. 3, if the identification pointer comprises the value or location of leaf node 320 and cannot progress any further, the system will update the identification pointer with the value of the parent node which is root node 310. The system will then return to step 412 to begin again with a subsequent token. As another example from FIG. 3, if the identification pointer comprises the value or location of leaf node 326 and cannot progress any further, the system will update the identification pointer with the value of the parent node at step 422, which is leaf node 314a. The value of this root node will be provided in steps 424/426, and the system can either end at 428 if there are no more tokens in the stream, or can progress to a subsequent token.

Figure 5:
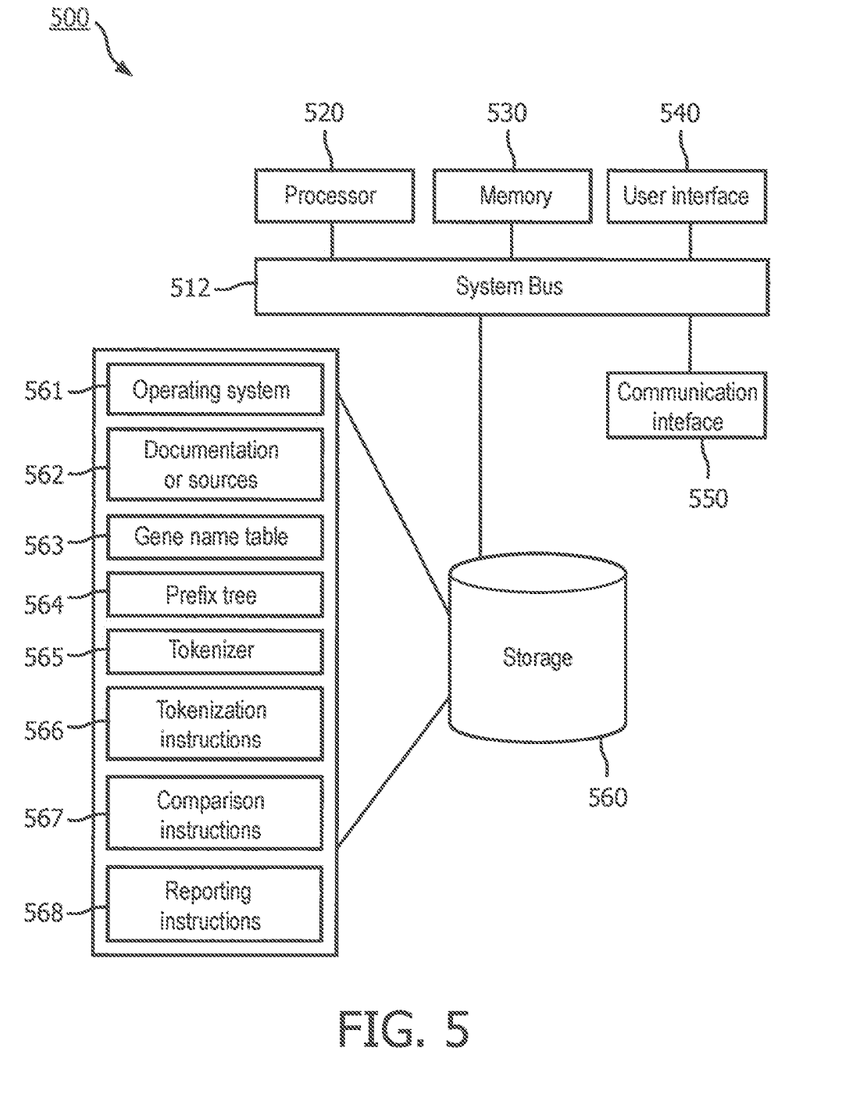
FIG. 5 is a schematic representation of a system for identifying canonical gene names, in accordance with an embodiment.

Referring to FIG. 5, in one embodiment, is a schematic representation of an gene name identification system 500 for generating a genome reference. System 500 may be any of the systems described or otherwise envisioned herein, and may comprise any of the components described or otherwise envisioned herein.

According to an embodiment, system 500 comprises one or more of a processor 520, memory 530, user interface 540, communications interface 550, and storage 560, interconnected via one or more system buses 512. It will be understood that FIG. 5 constitutes, in some respects, an abstraction and that the actual organization of the components of the system 500 may be different and more complex than illustrated.

According to an embodiment, system 500 comprises a processor 520 capable of executing instructions stored in memory 530 or storage 560 or otherwise processing data to, for example, perform one or more steps of the method. Processor 520 may be formed of one or multiple modules. Processor 520 may take any suitable form, including but not limited to a microprocessor, microcontroller, multiple microcontrollers, circuitry, field programmable gate array (FPGA), application-specific integrated circuit (ASIC), a single processor, or plural processors.

Memory 530 can take any suitable form, including a non-volatile memory and/or RAM. The memory 530 may include various memories such as, for example L1, L2, or L3 cache or system memory. As such, the memory 530 may include static random access memory (SRAM), dynamic RAM (DRAM), flash memory, read only memory (ROM), or other similar memory devices. The memory can store, among other things, an operating system. The RAM is used by the processor for the temporary storage of data. According to an embodiment, an operating system may contain code which, when executed by the processor, controls operation of one or more components of system 500. It will be apparent that, in embodiments where the processor implements one or more of the functions described herein in hardware, the software described as corresponding to such functionality in other embodiments may be omitted.

User interface 540 may include one or more devices for enabling communication with a user. The user interface can be any device or system that allows information to be conveyed and/or received, and may include a display, a mouse, and/or a keyboard for receiving user commands. In some embodiments, user interface 540 may include a command line interface or graphical user interface that may be presented to a remote terminal via communication interface 450. The user interface may be located with one or more other components of the system, or may located remote from the system and in communication via a wired and/or wireless communications network.

Communication interface 550 may include one or more devices for enabling communication with other hardware devices. For example, communication interface 550 may include a network interface card (NIC) configured to communicate according to the Ethernet protocol. Additionally, communication interface 550 may implement a TCP/IP stack for communication according to the TCP/IP protocols. Various alternative or additional hardware or configurations for communication interface 550 will be apparent.

Storage 560 may include one or more machine-readable storage media such as read-only memory (ROM), random-access memory (RAM), magnetic disk storage media, optical storage media, flash-memory devices, or similar storage media. In various embodiments, storage 560 may store instructions for execution by processor 520 or data upon which processor 520 may operate. For example, storage 560 may store an operating system 561 for controlling various operations of system 500. Storage 560 may also store one or more documents or sources 562, a gene name table 563, a prefix tree or data structure 564, and/or a tokenizer 565.

It will be apparent that various information described as stored in storage 560 may be additionally or alternatively stored in memory 530. In this respect, memory 530 may also be considered to constitute a storage device and storage 560 may be considered a memory. Various other arrangements will be apparent. Further, memory 530 and storage 560 may both be considered to be non-transitory machine-readable media. As used herein, the term non-transitory will be understood to exclude transitory signals but to include all forms of storage, including both volatile and non-volatile memories.

While gene name identification system 500 is shown as including one of each described component, the various components may be duplicated in various embodiments. For example, processor 520 may include multiple microprocessors that are configured to independently execute the methods described herein or are configured to perform steps or subroutines of the methods described herein such that the multiple processors cooperate to achieve the functionality described herein. Further, where one or more components of system 500 is implemented in a cloud computing system, the various hardware components may belong to separate physical systems. For example, processor 520 may include a first processor in a first server and a second processor in a second server. Many other variations and configurations are possible.

According to an embodiment, storage 560 of gene name identification system 500 may store one or more algorithms and/or instructions to carry out one or more functions or steps of the methods described or otherwise envisioned herein. For example, processor 520 may comprise, among other instructions, tokenization instructions 566, comparison instructions 567, and/or reporting instructions 568.

According to an embodiment, tokenization instructions 566 direct the system to tokenize a list or other gathering 563 of gene identifiers and canonical gene names, as described with regard to FIG. 2 and other methods as described or otherwise envisioned herein. For example, the tokenization instructions direct the system to generate a token stream from the list or other gathering of gene identifiers and canonical gene names according to tokenization logic set forth in the tokenization instructions, which can be utilized to generate the prefix tree or similar data structure 564 for analysis.

According to an embodiment, tokenization instructions 566 also direct the system to tokenize information from obtained or received documents or other sources 562 for use in identifying gene names within the sources. For example, the tokenization instructions direct the system to generate a token stream from documents or other sources 562 according to tokenization logic set forth in the tokenization instructions, which can be utilized to identify gene names within the sources.

As described herein or otherwise recognized, gene identifiers can come in an unlimited number of formats and variations, and thus suitable tokenization is a vital step in recognition and standardization of gene identifiers. Accordingly, the tokenization instructions are configured or designed to tokenize data in a manner that optimizes gene identifier recognition. A variety of tokenization methods may be utilized.

According to an embodiment, comparison instructions 567 direct the system to compare tokens to the prefix tree or similar data structure 564. The comparison instructions 567 direct the system to compare tokens, one at a time, to an appropriate location within data structure 564. For example, the comparison instructions direct the system to compare a token to one or more edges leading from a root node or a leaf node depending on the current location of a token. The comparison instructions also direct the system to update a value or location of an identification pointer with information about a root node or leaf node as a new node is identification from a comparison of a token and one or more edges. According to an embodiment, if there is no canonical gene name associated with a leaf node, and there are not further edges or matching edges extending from that leaf node, the comparison instructions can direct the system to update a value or location of the identification pointer with information about the most recent upstream or parent node until a leaf node associated with a canonical gene name (or the root node) is reached.

According to an embodiment, reporting instructions 568 direct the system to provide, record, and/or report a canonical gene name identified by one or more tokens in a token stream. For example, the reporting instructions can direct the system to provide the value or location of the identification pointer, which may be the determined canonical gene name, to another data point, a table, a report, or other location. For example, the system may create a table or list of all canonical gene names identified in a source. This could be created in memory or a database, displayed on a screen or other user interface, or otherwise provided. The report or list may also comprise the gene identifier or identifiers utilized to identify the canonical gene name, as well as information about the token or location of the token within the analyzed source. A report may be a visual display, a printed text, an email, an audible report, a transmission, and/or any other method of conveying information. The report may be provided locally or remotely, and thus the system or user interface may comprise or otherwise be connected to a communications system.

The one or more canonical gene names provided, recorded, and/or reported by the system has numerous applications. Indeed, the lightweight methods and systems described or otherwise envisioned herein afford ready accessibility, usability, extensibility, control, and portability to many clinical informatics applications.

For example, matching of patients to clinical trials for which they may be eligible often depends on the ability to search the text of each clinical trial description for genetic inclusion and exclusion criteria. The genetic status of patients may also require mining their textual medical records for the results of genetic tests, genotypic diagnoses, and prior genetics-specific treatments. The matching of patient genetic status with trial criteria requires accurate and efficient gene-name canonicalization, as well as matching variously-expressed genetic variants.

Additionally, the one or more canonical gene names may be useful in medical or other clinical settings. The system can serve to convert biomedical language to an agreed-upon standard in hospital and other health-related software systems. Such methods serve as valuable tools to any institution trying to modernize and make historical data actionable, such as queries to a system to return patients with a variant in a particular, normalized, gene.

More generally, gene name recognition and normalization enables one to understand the text within which genes are mentioned and discussed. For example, gene mentions participate in descriptions of genetic and chromosomal irregularities, which in turn contribute to recording the genotyping, diagnosing, and treating of healthcare patients. The knowledge in such textual records is more valuable when it is not only human-readable, but also machine-readable.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A computer-implemented method for standardizing gene nomenclature, the method comprising:
   receiving a source comprising one or more gene identifiers;
   tokenizing text from the source into a token stream;

comparing a first token from the token stream to a data structure generated from a database of gene identifiers and corresponding canonical gene name for each of a plurality of genes, the data structure comprising a prefix tree structure with a root node, a plurality of edges, and a plurality of leaf nodes;
  determining which of one or more edges extending from the root node to associated with first leaf node the first token matches;
  updating an identification pointer with a location of the first leaf node associated with the matching edge;
  determining which, if any, of one or more edges extending from the first leaf node to a second leaf node that a second, subsequent token from the token stream matches;
  updating, when the second token matches an edge extending from the first leaf node, the identification pointer with a location of the second leaf node associated with the matching edge;
  repeating the determining and updating with subsequent tokens from the token stream using any additional extending edges and leaf nodes until a subsequent token fails to match an edge extending from a leaf node or there is no edge extending from the leaf node; and
  providing, when a subsequent token fails to match an edge extending from a leaf node, or when there is no edge extending from the leaf node, an identification of a canonical gene name based on a most recent location from the identification pointer.

2. The method of claim 1, further comprising:
  generating a curated table of gene identifiers and associated canonical gene names;
  tokenizing the curated table into another token stream; and
  generating, using the other token stream, the prefix tree structure.

3. The method of claim 2, wherein tokenization of the curated table into the other token stream and the tokenization of text from the source into a token stream utilizes the same tokenization logic.

4. The method of claim 2, further comprising:
  generating a list of most common words in a language;
  comparing the list of most common words to the gene identifiers in the curated table; and
  identifying any gene identifiers found in the list of most common words.

5. The method of claim 1, wherein providing an identification of a canonical gene name based on the most recent location from the identification pointer comprises:
  updating the identification pointer with a location of a leaf node upstream of the most recent matching leaf node.

6. The method of claim 1, further comprising determining whether the identified canonical gene name is also common natural language word.

7. The method of claim 1, wherein tokenization comprises generating an acronym for every capitalized phrase in a document, and preventing or removing each occurrence of a generated acronym from the token stream.

8. The method of claim 1, wherein tokenization comprises generating a single token of each string of Roman letters, generating a single token of each run of numbers, and generating a single token with each Greek letter.

9. The method of claim 1, wherein providing an identification of a canonical gene name comprises information about a location of a gene identifier in the source.

10. A system for standardizing gene nomenclature, comprising:
  a source comprising one or more gene identifiers;
  a data structure generated from a database of gene identifiers and corresponding canonical gene name for each of a plurality of genes, the data structure comprising a prefix tree structure with a root node, a plurality of edges, and a plurality of leaf nodes; and
  a processor configured to: (i) tokenize text from the source into a token stream; (ii) compare a first token from the token stream to the data structure; (iii) determine which of one or more edges extending from the root node to associated first leaf node the first token matches; (iv) update an identification pointer with a location of the first leaf node associated with the matching edge; (v) determine which, if any, of one or more edges extending from the first leaf node to a second leaf node that a second, subsequent token from the token stream matches; (vi) update, when the second token matches an edge extending from the first leaf node, the identification pointer with a location of the second leaf node associated with the matching edge; (vii) repeat the determining and updating with subsequent tokens from the token stream using any additional extending edges and leaf nodes until a subsequent token fails to match an edge extending from a leaf node or there is no edge extending from the leaf node; and (viii) provide, when a subsequent token fails to match an edge extending from a leaf node, or when there is no edge extending from the leaf node, an identification of a canonical gene name based on a most recent location from the identification pointer.

11. The system of claim 10, wherein the processor is further configured to: generate a curated table of gene identifiers and associated canonical gene names; tokenize the curated table into another token stream; and generate, using the other token stream, the prefix tree structure.

12. The system of claim 10, wherein the processor is further configured to: generate a list of most common words in a language; compare the list of most common words to the gene identifiers in the curated table; and identify any gene identifiers found in the list of most common words.

13. The system of claim 10, wherein the processor is further configured to update the identification pointer with a location of a leaf node upstream of a most recent matching leaf node.

14. The system of claim 10, wherein tokenization comprises generating an acronym for every capitalized phrase in a document, and preventing or removing each occurrence of a generated acronym from the token stream.

15. The system of claim 10, wherein providing an identification of a canonical gene name comprises information about a location of a gene identifier in the source.

16. A tangible, non-transitory computer readable medium that stores instructions, which when executed by a processor, cause the processor to:
  receive a source comprising one or more gene identifiers;
  tokenize text from the source into a token stream;
  comparing a first token from the token stream to a data structure generated from a database of gene identifiers and corresponding canonical gene name for each of a plurality of genes, the data structure comprising a prefix tree structure with a root node, a plurality of edges, and a plurality of leaf nodes;
    determine which of one or more edges extending from the root node to associated with first leaf node the first token matches;
    update an identification pointer with a location of the first leaf node associated with the matching edge;

determine which, if any, of one or more edges extending from the first leaf node to a second leaf node that a second, subsequent token from the token stream matches;

update, when the second token matches an edge extending from the first leaf node, the identification pointer with a location of the second leaf node associated with the matching edge;

repeat the determining and updating with subsequent tokens from the token stream using any additional extending edges and leaf nodes until a subsequent token fails to match an edge extending from a leaf node or there is no edge extending from the leaf node; and provide, when a subsequent token fails to match an edge extending from a leaf node, or when there is no edge extending from the leaf node, an identification of a canonical gene name based on a most recent location from the identification pointer.

17. The tangible, non-transitory computer readable medium of claim 16, wherein when executed by the processor, the instructions further cause the processor to:

generate a curated table of gene identifiers and associated canonical gene names;

tokenize the curated table into another token stream; and generating, using the other token stream, the prefix tree structure.

18. The tangible, non-transitory computer readable medium of claim 17, wherein tokenization of the curated table into the other token stream and the tokenization of text from the source into a token stream utilizes the same tokenization logic.

19. The tangible, non-transitory computer readable medium of claim 16, wherein when executed by the processor, the instructions further cause the processor to:

generate a list of most common words in a language;

compare the list of most common words to the gene identifiers in the curated table; and identify any gene identifiers found in the list of most common words.

20. The tangible, non-transitory computer readable medium of claim 16, wherein when executed by the processor, the instructions further cause the processor to:

update the identification pointer with a location of a leaf node upstream of a most recent matching leaf node.

* * * * *